United States Patent
Storr et al.

(10) Patent No.: US 11,103,624 B2
(45) Date of Patent: Aug. 31, 2021

(54) PERMSELECTIVE MEMBRANE FOR TREATING VASCULAR CALCIFICATIONS IN CHRONIC HEMODIALYSIS PATIENTS

(71) Applicants: GAMBRO LUNDIA AB, Lund (SE); CHARITÉ UNIVERSITÄTSMEDIZIN BERLIN, Berlin (DE)

(72) Inventors: Markus Storr, Lund (SE); Bernd Krause, Lund (SE); Ralf Schindler, Berlin (DE); Daniel Zickler, Berlin (DE); Bjoern Hegner, Berlin (DE)

(73) Assignees: GAMBRO LUNDIA AB, Lund (SE); CHARITÉ UNIVERSITÄTSMEDIZIN BERLIN, Berlin (DE)

( * ) Notice: Subject to any disclaimer, the term of this patent is extended or adjusted under 35 U.S.C. 154(b) by 806 days.

(21) Appl. No.: 15/956,080

(22) Filed: Apr. 18, 2018

(65) Prior Publication Data
US 2018/0228958 A1 Aug. 16, 2018

Related U.S. Application Data

(63) Continuation of application No. 14/511,329, filed on Oct. 10, 2014, now Pat. No. 9,974,895.

(30) Foreign Application Priority Data

Oct. 17, 2013 (EP) .................................. 13004968

(51) Int. Cl.
*A61M 1/16* (2006.01)
*B01D 63/02* (2006.01)
(Continued)

(52) U.S. Cl.
CPC ................ *A61M 1/16* (2013.01); *A61K 35/14* (2013.01); *B01D 63/021* (2013.01); *B01D 69/08* (2013.01);
(Continued)

(58) Field of Classification Search
CPC ........ A61M 1/16; A61M 1/1621; A61M 1/34; A61M 1/36; A61M 2202/0014;
(Continued)

(56) References Cited

U.S. PATENT DOCUMENTS

| | | | |
|---|---|---|---|
| 9,974,895 B2 * | 5/2018 | Storr | B01D 71/68 |
| 2006/0144782 A1 * | 7/2006 | Buck | A61M 1/3403 210/500.23 |
| 2012/0305487 A1 * | 12/2012 | Beck | B01D 69/08 210/647 |

OTHER PUBLICATIONS

"Inflammation modifies the pattern and the function of Toll-like receptors expressed by human mesenchymal stromal cells", Mar. 2010, Human Immunology, vol. 71, No. 3, pp. 235-244.*

* cited by examiner

*Primary Examiner* — Philip R Wiest
(74) *Attorney, Agent, or Firm* — Barnes & Thornburg LLP

(57) ABSTRACT

The present disclosure relates to a hemodialysis membrane for the treatment of vascular calcification in hemodialysis patients, especially in chronic hemodialysis patients. The present disclosure further relates to methods of treating vascular calcification in hemodialysis patients, wherein the hemodialysis membrane is characterized in that it comprises at least one hydrophobic polymer and at least one hydrophilic polymer and in that it has a MWRO of between 15 and 20 kD and a MWCO of between 170-320 kD or that the hemodialysis membrane comprises at least one hydrophobic polymer and at least one hydrophilic polymer and has a
(Continued)

MWRO of between 8.5 kD and 14.0 kD and a MWCO of between 55 kD and 130 kD.

20 Claims, 7 Drawing Sheets

(51) Int. Cl.
*B01D 69/08* (2006.01)
*B01D 69/14* (2006.01)
*B01D 71/68* (2006.01)
*A61K 35/14* (2015.01)
*B01D 61/24* (2006.01)

(52) U.S. Cl.
CPC ........... B01D 69/141 (2013.01); B01D 71/68 (2013.01); *A61M 2202/0014* (2013.01); *B01D 61/243* (2013.01); *B01D 2325/38* (2013.01)

(58) Field of Classification Search
CPC .... B01D 63/021; B01D 69/08; B01D 69/141; B01D 61/243; B01D 71/68; B01D 2325/38; A61K 35/14
See application file for complete search history.

PERMSELECTIVE MEMBRANE FOR TREATING VASCULAR CALCIFICATIONS IN CHRONIC HEMODIALYSIS PATIENTS

CROSS-REFERENCE TO RELATED APPLICATIONS

This application is a continuation of U.S. patent application Ser. No. 14/511,329, filed Oct. 10, 2014, which claims the benefit of European Patent Application Ser. No. 13004968.7, filed Oct. 17, 2013, the disclosures of both which are hereby incorporated herein by reference.

TECHNICAL FIELD

The present disclosure relates to a hemodialysis membrane for the treatment of vascular calcification in hemodialysis patients, especially in chronic hemodialysis patients. The present disclosure further relates to methods of treating vascular calcification in hemodialysis patients, wherein the hemodialysis membrane is characterized in that it comprises at least one hydrophobic polymer and at least one hydrophilic polymer and in that it has a MWRO of between 15 and 20 kD and a MWCO of between 170-320 kD, or, in the alternative, has a MWRO of between 8.5 and 14 kD and a MWCO of between 55 kD and 130 kD.

DESCRIPTION OF THE RELATED ART

Patients with impaired renal function due to chronic kidney diseases face one of the highest risks for cardiovascular morbidity and death that continuously increases as kidney function declines. This is true for patients with pre-end-stage renal failure, on dialysis or after successful renal transplantation. It is the most common cause for death in patients with a functional allograft, and prevents many dialysis patients from being engrafted (Goldsmith et al. (2001): "Coronary artery disease in patients with renal failure", *Int J Clin Pract* 55, 196-210). The prevailing metabolic milieu in moderate-to-severe chronic renal failure and on dialysis strongly seems to favor an increased rate of atherosclerosis and atherosclerotic/thrombotic events in these patients. There is now evidence that vascular smooth muscle cells can become chondrocyte or osteoblast-like and lay down and mineralize collagen and non-collagenous proteins in arteries. Resulting vascular calcification remains one of the major unsolved problems in uremic patients. Arterial calcium load seems to be a strong predictor for cardiovascular complications in this population.

Vascular calcification is common in physiologic and pathologic conditions such as aging, diabetes, dyslipidemia, genetic diseases, and diseases with disturbances of calcium metabolism. However, in CKD patients, vascular calcification is even more common, developing early and contributing to the markedly increased cardiovascular risk. Increased knowledge about the mechanisms of calcification together with improved imaging techniques have provided evidence that vascular calcification should be divided into two distinct entities according to the specific site of calcification within the vascular wall. Intimal calcification is advanced atherosclerosis, occurring in medium-to-large conduit arteries without smooth muscle cells. Plaques develop and arterial occlusion occurs. Medial calcification, known also as Mönckeberg's arteriosclerosis, occurs in elastin fibers around smooth muscle cells in the absence of atherosclerosis or inflammation and is seen primarily in chronic renal failure or diabetes. It is typically less occlusive of the arterial lumen than intimal calcification. (Nakamura et al (2009): "Coronary Calcification in Patients with chronic kidney disease and coronary artery disease". *Clin J Am Soc Nephrol* 4, 1892-1900). Also, medial calcification occurs in arteries of any size, including small arteries in which atherosclerosis does not occur. Renal failure increases the extent of calcification in atherosclerotic plaques, but the effect on medial calcification is probably greater as it rarely occurs in individuals without renal insufficiency under the age of 60 years. The histological prevalence of medial calcification in radial arteries was 45-fold greater in patients with CKD compared with those without CKD (O'Neill et al. (2010): "Recent progress in the treatment of vascular calcification". *Kidney Int.* 78(12), 1232-1239).

In general, the presence of vascular calcifications in end-stage renal disease (ESRD) patients is associated with increased stiffness of large, capacitive, elastic-type arteries like the aorta and common carotid artery (CCA) (Blacher et al. (2001): "Arterial Calcifications, Arterial Stiffness, and Cardiovascular Risk in End-Stage Renal Disease". *Hypertension* 38, 938-942), together with higher pulse wave velocity (PWV), earlier return of wave reflections from the periphery to the ascending aorta during systole and abnormal increase of aortic systolic blood pressure, with reduced diastolic blood pressure and high pulse pressure. In the general population and in patients with CKD, electron-beam computed tomography (EBCT) has proven coronary artery calcification (CAC) as a potent predictor of cardiac events. Both the prevalence and intensity of CAC are increased in patients with CKD.

Traditional cardiac risk factors do not appear to entirely account for the elevated cardiovascular morbidity seen in advanced CKD. Hyperphosphatemia, elevated Ca×P product, and hyperparathyroidism have been associated with cardiovascular disease (CVD) risk and mortality in advanced CKD. In addition, uremia is believed to confer nontraditional CVD risks such as, for example, a proinflammatory state and dysregulation of calcification inhibitors and inducers.

Calcification in patients with end-stage renal disease (ESRD) was previously believed to occur as a result of passive mineral deposition processes. Although the pathophysiology is not completely understood, it is clear that it is a multifactorial process involving altered mineral metabolism, as well as changes in systemic and local factors that can promote or inhibit vascular calcification, and all of these are potential therapeutic targets. Molecular Mechanisms involved in vascular calcification are described, for example, in Mizobuchi et al. (2009): "Vascular Calcification: The Killer of Patients with Chronic Kidney Disease", *J Am Soc Nephrol* 20, 1454, namely ectopic osteogenesis and elastin degradation. Inducers of vascular calcification are also reviewed in Mizobuchi et al. (2009): "Vascular Calcification: The Killer of Patients with Chronic Kidney Disease", *J Am Soc Nephrol* 20, 1453-1464, where it is stated that compared with the general population, patients with CKD have a disproportionately high occurrence of vascular calcification. One hypothesis to account for this is the altered $Ca^{2+}$ and $P^{2-}$ metabolism seen in these patients. This is the most important contributor to the progression of vascular calcification in the uremic condition. Another factor mentioned are uremic toxins. Uremic serum was found to upregulate the expression of, for example, Cbfa1/Runx2 and its target protein OPN, and increases secretion of a mediator of osteoblastic differentiation, BMP-2, resulting in the mineralization of VSMCs into osteoblast-like cells, see also Moe et al. (2008), FIG. 1. Mizobuchi et al. also mention oxidative stress and inflammation and other inducers such as leptin. The bone proteins osteonectin, osteopontin, bone sialoprotein, type I collagen, and alkaline phosphatase have also been identified in multiple sites of extraskeletal calcification. Interestingly, in cell culture, vascular smooth muscle cells and vascular pericytes are capable of producing these same boneforming transcription factors and proteins, and can be induced to do so with high concentrations of phosphorus, uremic serum, high glucose, oxidized lipids, and several other factors (Moe et al. (2008): "Mechanisms of Vascular Calcification in Chronic Kidney Disease", *J Am Soc Nephrol* 19, 213-216.

Therefore, current therapeutic approaches are directed to preventing disordered bone and mineral metabolism in advanced kidney disease and mainly involve lowering the circulating levels of both phosphate and calcium. The efficacy of compounds that specifically target calcification, such as bisphosphonates and thiosulfate, has been shown in animals but only in small numbers of humans, and safety remains an issue (O'Neill et al. (2010): "Recent progress in the treatment of vascular calcification". *Kidney Int.* 78(12), 1232-1239). Additional therapies, such as pyrophosphate, vitamin K, and lowering of pH, are supported by animal studies, but are yet to be investigated in further detail (O'Neill et al. (2010)). In any case, potential anticalcification therapies always carry the risk of adversely acting on normal calcification, for example in bones and teeth.

Interestingly, not all dialysis patients seem to develop arterial calcifications, despite similar exposure to these risk factors, and importantly, do not develop calcification with increased duration of dialysis (Moe et al. (2008)). For the efficient treatment of CKD patients, it is therefore helpful to which patients have a high risk for a cardiovascular event. Patients with calcification having a higher risk for future coronary events than an age-gender-specific percentile ranking can then be treated with available therapies. The Kidney Disease Improving Global Outcomes (KDIGO) suggests (see *Kidney International* (2009) (Suppl 113), S1-S2) that patients with CKD stages 3-5 with known vascular/valvular calcification should generally be considered at highest cardiovascular risk. Coronary artery calcification score (CACS) may be used as a quantitative assessment of calcified atherosclerosis which is detectable by electron-beam (EBCT) or multislice computed tomography (CT). The score which is also referred to as Agatston score is calculated using a weighed value assigned to the highest density of calcification in a given coronary artery. Details on how the Agatston score as used herein can be determined and analyzed are given in Halliburton et al. (2010): "Noninvasive quantification of coronary artery calcification: methods and prognostic value", *Cleve Clin J Med.* 69 (suppl. 3), S6-S11. A more elaborate method to determine the Agatston score of a patient is shown in van der Bijl et al. (2010), *AJR* 195, 1299-1305. An Agatston score of 0 is normal. In general, the higher the score, the more likely it is to have a coronary heart disease (CHD). A score of 0 to 10 is associated to a low risk, a score of 11 to 100 to an intermediate risk. A score of more than 100 (>100) describes an intermediate to high risk. A score of more than 400 (>400) describes persons with a very high risk (Halliburton et al. (2010)).

So far, current therapeutic approaches are, apart from nutritional aspects, based mainly on a certain medication of the patients in need of a treatment. The dialysis treatment, in contrast, has mainly been discussed with regard to the risks it imposes on a CKD patient and the development of vascular calcification. However, because of the risks and drawbacks associated with the compound based anticalcification therapies directed to preventing disordered bone and mineral metabolism in advanced kidney disease, it would clearly be desirable to devise a dialysis system which is able to lower or reduce calcification in CKD patients already during the extracorporeal treatment and before vascular calcification develops. If a system can be devised which is able to reduce the onset of calcification in CKD patients or reduces existing calcification in patients who already have to undergo medication, said medication and potential side effects related thereto could be reduced or omitted completely.

Currently available membranes and filters for use in hemodialysis, hemodiafiltration or hemofiltration could so far not contribute effectively to avoiding or reducing vascular calcification in uremic patients. For the avoidance of doubt, if not expressly indicated otherwise, the expression "hemodialysis" as used herein encompasses hemodialysis, hemodiafiltration and hemofiltration methods. Based on the findings on molecular mechanisms involved in vascular calcification as described above and reviewed, for example, in Mizobuchi et al. (2009), the present inventors have focused their attention on the key mediators for the mineralization of cells in the vessel wall and on methods for the removal of such mediators rather than addressing calcification problems by administering inhibitors of such mediators. As a result of their studies, the inventors have found that newly developed membranes, so-called high cut-off membranes can be used for eliminating from CKD patients in need said pro-calcifying mediators which induce and/or promote calcification. It was found as a consequence that calcification can be reduced or delayed by using said high cut-off membranes in the extracorporeal hemodialysis treatment of uremic patients.

In general, dialysis membranes are designed to accomplish the removal of uremic toxins and excess water from the blood of patients with chronic renal failure while balancing the electrolyte content in the blood with the dialysis fluid. Uremic toxins are usually classified according to their size and physicochemical characteristics in small water-soluble compounds (e.g., urea and creatinine), protein-bound solutes (e.g., p-cresyl sulfate) and middle molecules (e.g., b2-microglobulin and interleukin-6) (1-4). While the removal of small molecules takes place mainly by diffusion due to concentration differences between the blood stream and the dialysis fluid flow, the removal of middle molecules is mainly achieved by convection through ultrafiltration. The degree of diffusion and convection depends on the treatment mode (hemodialysis, hemofiltration or hemodiafiltration) as well as on the membrane type (low-flux, high-flux, protein leaking, or high cut-off membranes). The sieving property of a membrane, i.e., its permeability to solutes, is determined by the pore size and sets the maximum size for the solutes that can be dragged through the membrane with the fluid flow. The sieving coefficient for a given substance could be simply described as the ratio between the substance concentration in the filtrate and its concentration in the feed (i.e., the blood or plasma), and is therefore a value between 0 and 1. Assuming that the size of a solute is proportional to its molecular weight, a common way to illustrate the properties of membranes is by creating a sieving curve, which depicts the sieving coefficient as a function of the molecular weight. The molecular weight cut-off (MWCO) is defined as the molecular weight where the sieving coefficient is 0.1 (FIG. 1). The sieving curve determined for a polydisperse dextran mixture can be considered a standard characterization technique for a membrane. Conventional dialysis membranes are classified as low-flux or high-flux, depending on their permeability. A third group, called protein leaking membranes, is also available on some markets. These three membrane groups were described in a review by Ward (2005), *J Am Soc Nephrol* 16, 2421-2430. Lately a fourth type has emerged, the above-mentioned high cut-off membranes, which have particular characteristics (Boschetti-de-Fierro et al. (2013): "Extended characterization of a new class of membranes for blood purification: The high cut-off membranes", *Int J Artif Organs* 36(7), 455-463). A concise summary of the general classification and performance of said membranes as is shown in Table I of Boschetti-de-Fierro et al. (2013) and shall be valid also for describing the present invention. The latest step in membrane development is a membrane type which in terms of classification could be positioned in between the so-called high flux and the high cut-off membranes. Said membranes are therefore also referred to as "medium cut-off" membranes (see also Table II). These membranes and how they can be prepared are described in detail in European Patent Application No. 14154175.5.

and treatment of anemia (US 2012/0305487 A1), the most explored therapy to date being the treatment of myeloma kidney (U.S. Pat. No. 7,875,183 B2). In this case, the removal of the free light chains in patients with multiple myeloma on chemotherapy has allowed the recovery of kidney function in a significant number of patients. Due to the loss of up to 40 g of albumin per session with the above-mentioned dialyzers, high cut-off membranes have been used for acute applications, although some physicians have contemplated benefits of using them in chronic applications, possibly in conjunction with albumin substitution.

The expression "molecular weight cut-off" or "MWCO" or "nominal molecular weight cut-off" as used herein is a value for describing the retention capabilities of a membrane and refers to the molecular mass of a solute where the membranes have a rejection of 90% (see above and FIG. 1), corresponding to a sieving coefficient of 0.1. The MWCO can alternatively be described as the molecular mass of a solute, such as, for example, dextrans or proteins where the

TABLE I

General classification and typical performance of hemodialysis membranes

| Dialyzer type | Water permeability[a] ml/(m²hmmHg) | Sieveing Coefficient[b] | | FLC Clearance[c] | | Album in Loss (g)[d] |
|---|---|---|---|---|---|---|
| | | β2-Micro-globulin | Albumin | Kappa | Lambda | |
| Low-flux | 10-20 | — | <0.01 | — | — | 0 |
| High-flux | 200-400 | 0.7-0.8 | <0.01 | <10 | <2 | <0.5 |
| Protein leaking | 50-500 | 0.9-1.0 | 0.02-0.03 | — | — | 2-6 |
| High cut-off | 1100 | 1.0 | 0.2 | 38 | 33 | 28 |

[a] with 0.9 wt.-% sodium chloride at 37 ± 1° C. and $Q_B$ 100-500 ml/min
[b] according to EN1283 with $Q_B$ max and UF 20%
[c] Serum Free Light Chains, Clearance in vitro, $Q_B$ 250 ml/min and $Q_D$ 500 ml/min, UF 0 ml/min, Bovine Plasma, 60 g/l, 37° C., Plasma Level: human κ 500 mg/l, human λ 250 mg/l. All clearances in ml/min, measured for membrane areas between 1.7 and 2.1 m²
[d] measured in conventional hemodialysis, after a 4-h session, with $Q_B$ 250 ml/min and $Q_D$ 500 ml/min, for membrane areas between 1.7 and 2.1 m²

The most evident difference among the types of membranes is their position along the molecular weight axis (FIG. 2). High-flux membranes have a sieving curve more similar to that of the glomerular membrane, removing toxins of small molecular weight such as urea and also allowing some removal of relatively large toxins, such as β2-microglobulin and myoglobin. High cut-off membranes show a sieving curve located at higher molecular weights than that for the glomerular membrane. Although the high cut-off sieving profile resembles that of the glomerular membrane up to 20 kDa, the high cut-off membranes are open toward molecular weights higher than 20 kDa. This means that the high cut-off membranes allow some passage of proteins. WO 2004/056460 already discloses certain early high cut-off membranes which could be used for the treatment of sepsis in dialyzers by eliminating sepsis-associated inflammatory mediators. Advanced dialyzers with high cut-off membranes which are currently on the market are, for example, HCO1100®, septeX™ and Theralite®, all available from Gambro Lundia AB. Known uses of high cut-off membranes include treatment of sepsis, chronic inflammation (EP 2 161 072 A1), amyloidosis and rhabdomyolysis membranes allow passage of 10% of the molecules. The shape of the curve depends, for example, on the pore size distribution and is thus linked to the physical form of appearance of the membrane.

As already mentioned, sieving curves give relevant information in two dimensions: the shape of the curve describes the pore size distribution, while its position on the molecular weight axis indicates the size of the pores. Molecular weight cut-off (MWCO) limits the analysis of the sieving curve to only one dimension, namely to the size of the pores where the sieving coefficient is 0.1. To enhance membrane characterization the molecular weight retention onset (MWRO) is used herein for characterizing high cut-off and medium cut-off membranes. The MWRO is defined as the molecular weight at which the sieving coefficient is 0.9, as schematically shown in FIG. 1. It is analogous to the MWCO and describes when the sieving coefficient starts to fall from 1 to 0. Defining two points on the sieving curves allows a better characterization of the sigmoid curve, giving an indication of the pore sizes and also of the pore size distribution. The expression "molecular weight rejection onset" or "MWRO" or "nominal molecular weight rejection onset", as used herein, therefore refers to the molecular mass of a solute where the membranes have a rejection of 10%, or, in other words, allow passage of 90% of the solute, corresponding to a sieving coefficient of 0.9.

The use of dextran sieving curves together with the respective MWCO and MWRO values based thereon allows differentiating the existing dialyzer types low-flux, high-flux, protein leaking, medium cut-off or high cut-off (FIG. 3). Compared to the high-flux dialyzers, which are the standard for current dialysis treatment, the low-flux dialyzers are depicted in a group with low MWRO and MWCO. The other two families—protein leaking and high cut-off dialyzers—have different characteristics. While the protein leaking dialyzers are mainly characterized by a high MWCO and a low MWRO, the high cut-off family can be strongly differentiated due to the high in vitro values for both MWRO and MWCO (Table II).

TABLE II

General classification of hemodialysis membranes based on dextran sieving

| Dialyzer type | Structural Characteristics | | |
|---|---|---|---|
| | MWRO [kDa] | MWCO [kDa] | Pore radius [nm] |
| Low-flux | 2-4 | 10-20 | 2-3 |
| High-flux | 5-10 | 25-65 | 3.5-5.5 |
| Protein leaking | 2-4 | 60-70 | 5-6 |
| High cut-off | 15-20 | 170-320 | 8-12 |
| Medium cut-off | 8.5-14.0 | 55-130 | 5.5 < pore radius < 8.0 |

The applicants have found that high cut-off membranes as defined above and in Table II as well as medium cut-off membranes as defined above and described in further detail in EP 14154175.5 can be used to effectively treat vascular calcification in chronic hemodialysis patients. Especially the high permeability of the high cut-off membranes but also the characteristics of the medium cut-off membranes seem to allow for an increased clearance of relevant mediators in comparison to the high-flux dialyzers which currently are the standard for treating chronic hemodialysis patients. More specifically, even though the uremic milieu is characterized by a multitude of known and so far unidentified substances, the inventors were able to show a reduction of mediators in the serum of patients having been treated with high cut-off or medium cut-off membranes, which serum otherwise could be shown to induce osteoblastic phenotype and osteoblastic differentiation in mesenchymal stem cells (MSC).

SUMMARY OF THE INVENTION

It is the object of the present invention to provide for a method of treating vascular calcification in a hemodialysis patient, comprising withdrawing and bypassing the blood from the patient in a continuous flow into contact with one face of an hemodialysis membrane, simultaneously passing dialysate solution in a continuous flow on an opposite face of the hemodialysis membrane to the side of the hemodialysis membrane in contact with the blood, the flow of the dialysate solution being countercurrent to the direction of flow of blood, and returning the blood into the patient, wherein the hemodialysis membrane is characterized in that it comprises at least one hydrophobic polymer and at least one hydrophilic polymer and in that it has a MWRO of between 15 and 20 kD and a MWCO of between 170-320 kD or in that it has a MWRO of between 8.5 kD and 14.0 kD and a MWCO of between 55 and 130 kD. The MWRO and MWCO for a given membrane is based on dextran sieving experiments before blood contact of the membrane as described by Boschetti-de-Fierro et al. (2013)(see "Materials and Methods" section of the reference).

DETAILED DESCRIPTION

Figure 1:
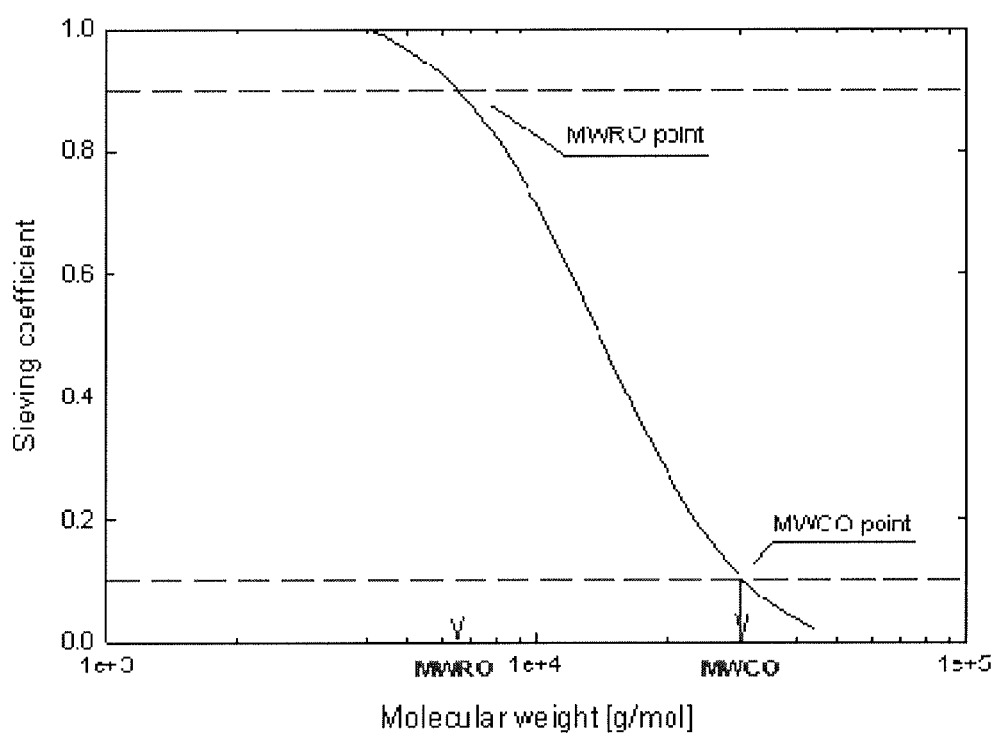
FIG. 1 is a representation of a dextran sieving curve where the values of molecular weight retention onset (MWRO, achieved at SC=0.9) and molecular weight cut-off (MWCO, achieved at SC=0.1) are illustrated.

Patients with impaired renal function due to chronic kidney diseases face one of the highest risks for cardiovascular morbidity and death that continuously increases as kidney function declines. This is true for patients with pre-end-stage renal failure, on dialysis or after successful renal transplantation.

The present disclosure therefore relates to a high cut-off or medium cut-off hemodialysis membrane for the treatment of vascular calcification in hemodialysis patients, especially in chronic hemodialysis patients and especially in a CKD stage 3-5 patient having an Agatston score of more than 11. The method comprises withdrawing and bypassing the blood from the patient in a continuous flow into contact with one face of an hemodialysis membrane, simultaneously passing dialysate solution in a continuous flow on an opposite face of the hemodialysis membrane to the side of the hemodialysis membrane in contact with the blood, the flow of the dialysate solution being countercurrent to the direction of flow of blood, and returning the blood into the patient, wherein the hemodialysis membrane is characterized in that it comprises at least one hydrophobic polymer and at least one hydrophilic polymer and in that it has a MWRO of between 15 and 20 kD and a MWCO of between 170-320 kD. Alternatively, the membrane has a MWRO of between 8.5 kD and 14.0 kD and a MWCO of between 55 and 130 kD. The MWRO and MWCO for a given membrane is based on dextran sieving experiments as described by Boschetti-de-Fierro et al. (2013) (see "Materials and Methods" section of the reference) and refers to values obtained before blood contact of the membrane.

As described before in this document, patients with CKD have a disproportionately high occurrence of vascular calcification. One hypothesis to account for this is the altered $Ca^{2+}$ and $P^{2-}$ metabolism seen in these patients. Another factor mentioned is uremic toxins and uremic serum was found to upregulate the expression of, for example, Cbfa1/Runx2 and its target protein OPN, and increases secretion of a mediator of osteoblastic differentiation, BMP-2, resulting in the mineralization of VSMCs into osteoblast-like cells. Oxidative stress and inflammation and other inducers such as leptin are also discussed as possible inducers. The bone proteins osteonectin, osteopontin, bone sialoprotein, type I collagen, and alkaline phosphatase have also been identified in multiple sites of extraskeletal calcification. Interestingly, in cell culture, vascular smooth muscle cells and vascular pericytes are capable of producing these same boneforming transcription factors and proteins, and can be induced to do so with high concentrations of phosphorus, uremic serum, high glucose, oxidized lipids, and several other factors (Moe et al. (2008): "Mechanisms of Vascular Calcification in Chronic Kidney Disease", J Am Soc Nephrol 19, 213-216.

As cells of mesenchymal origin including endothelial and vascular smooth muscle cells are prime targets of uremic solutes, mesenchymal stromal cells (MSCs) as common progenitors of both are a suitable model to identify mechanisms by which the uremic milieu interior may disturb vascular health. The model can also be used to determine the effect of the use of high cut-off membranes/dialyzers on vascular calcification indicators in the uremic retention solutes. For the present invention, effects of 64 individual uremic retention solutes (URS) on osteoblastic transformation of MSCs were systematically studied in order to identify therapeutic strategies feasible for targeting of vascular calcification.

Bone marrow derived MSCs were separately treated with 64 individual URS at uremic concentrations in osteoblastic induction medium. Osteoblastic differentiation was measured by alkaline phosphatase activity, western blot, immunocytochemistry, and calcium deposition. In an additional translational approach, osteoblastic potential of serum obtained upon high cut-off dialyzer treatment was compared to that obtained upon conventional dialysis. It was found in said approach that substance removal with high cut-off dialyzers had favorable effects on the attenuation of osteoblastic differentiation and calcium deposition by MSCs. The findings emphasize importance of larger molecules, sometimes also referred to as "middle molecules", in mediating uremic calcifying MSC phenotype. Since conventional dialysis strategies fail to effectively remove this group of URS, targeted dialysis modalities, possibly in combination with specific pharmacologic interventions were found to be useful for addressing the unsolved problem of vascular calcification in chronic kidney diseases.

Figure 4:
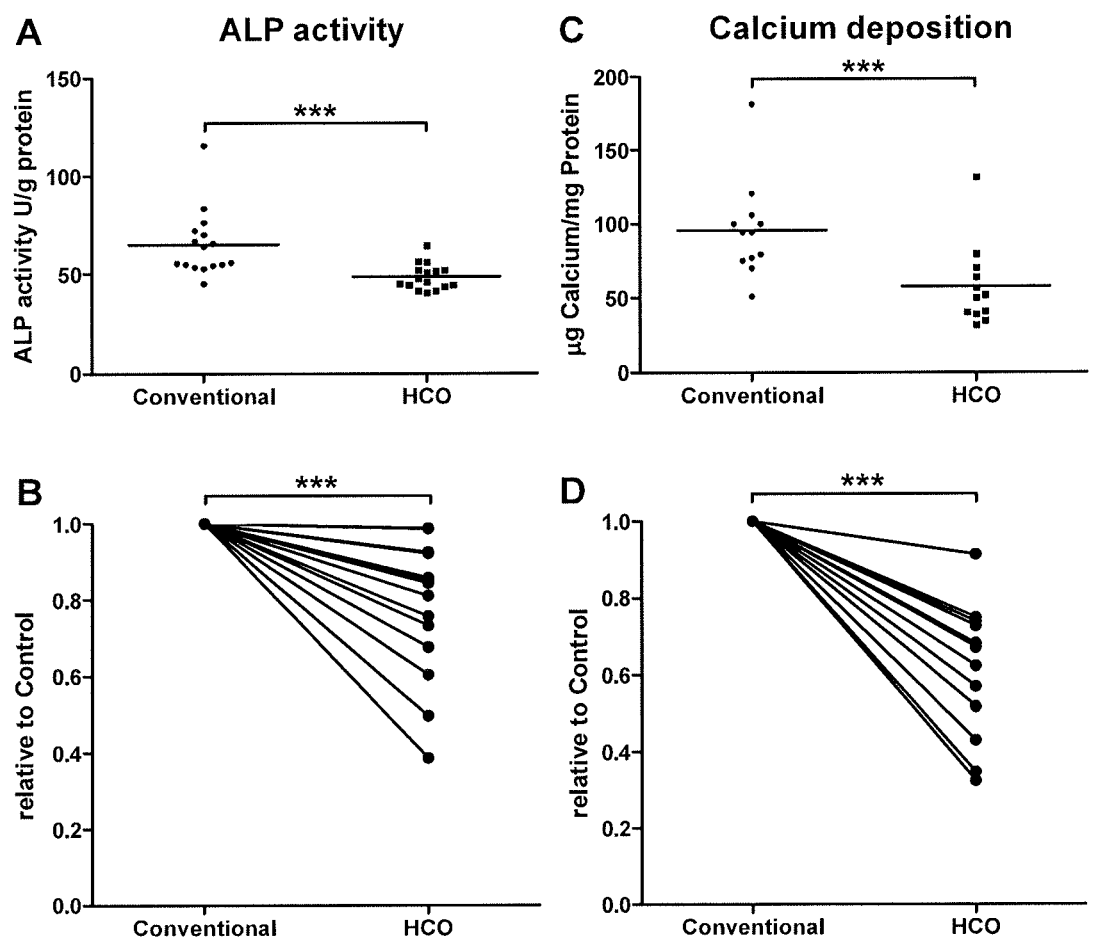
FIG. 4 depicts the effect of dialysis with high cut-off membranes on serum induced osteoblast differentiation and calcification of mesenchymal stromal cells (MSC). MSCs were induced with osteoblast induction medium containing serum from dialysis patients treated either with conventional high-flux dialyzers (Conventional) or from the same patients after a 3 weeks course of dialysis with high cut-off membranes (HCO). (A) Alkaline phosphatase (ALP) activity normalized to protein content measured on single-patient level (n-16). (B) ALP activity measurements from the same patients with conventional treatment set 1.0. (C) Quantification of deposited calcium normalized to protein content. Sera from a total of 16 patients were combined to 3 different serum pools for both treatment modalities. Each serum pool was applied to 4 MSC preparations from different healthy donors. (D) Calcium measurements from the same serum pools and cell preparations with conventional treatment set 1.0. ***P<0.001.

In the present invention, the question was addressed, if maintenance dialysis with membranes characterized by a higher molecular weight cut-off and consequently a greater capacity for the removal of larger molecules compared to conventional high flux dialyzers could improve serum composition and reduce its pro-osteoblastic and pro-calcifying effect on MSCs. Serum from patients that had been dialyzed with high cut-off membranes for 3 weeks with serum from the same patients obtained during a period when they had been dialyzed with conventional high-flux membranes (Example 3). Overall, the potential for induction of osteoblastic differentiation in MSCs was reduced when serum was obtained during HCO dialysis compared to conventional high-flux dialysis as indicated by alkaline phosphatase (ALP) activity (48.67±1.6 U/g protein versus 65.02±4.2 U/g protein; FIG. 4A). This effect was detectable in the paired serum samples of each patient (FIG. 4B). Finally, MSCs treated with serum from patients treated with high cut-off membranes deposited 40% less calcium compared to serum obtained during a period of conventional dialysis (FIG. 4C). Reduced calcification was consistently present in each single experiment (FIG. 4D).

Figure 5:
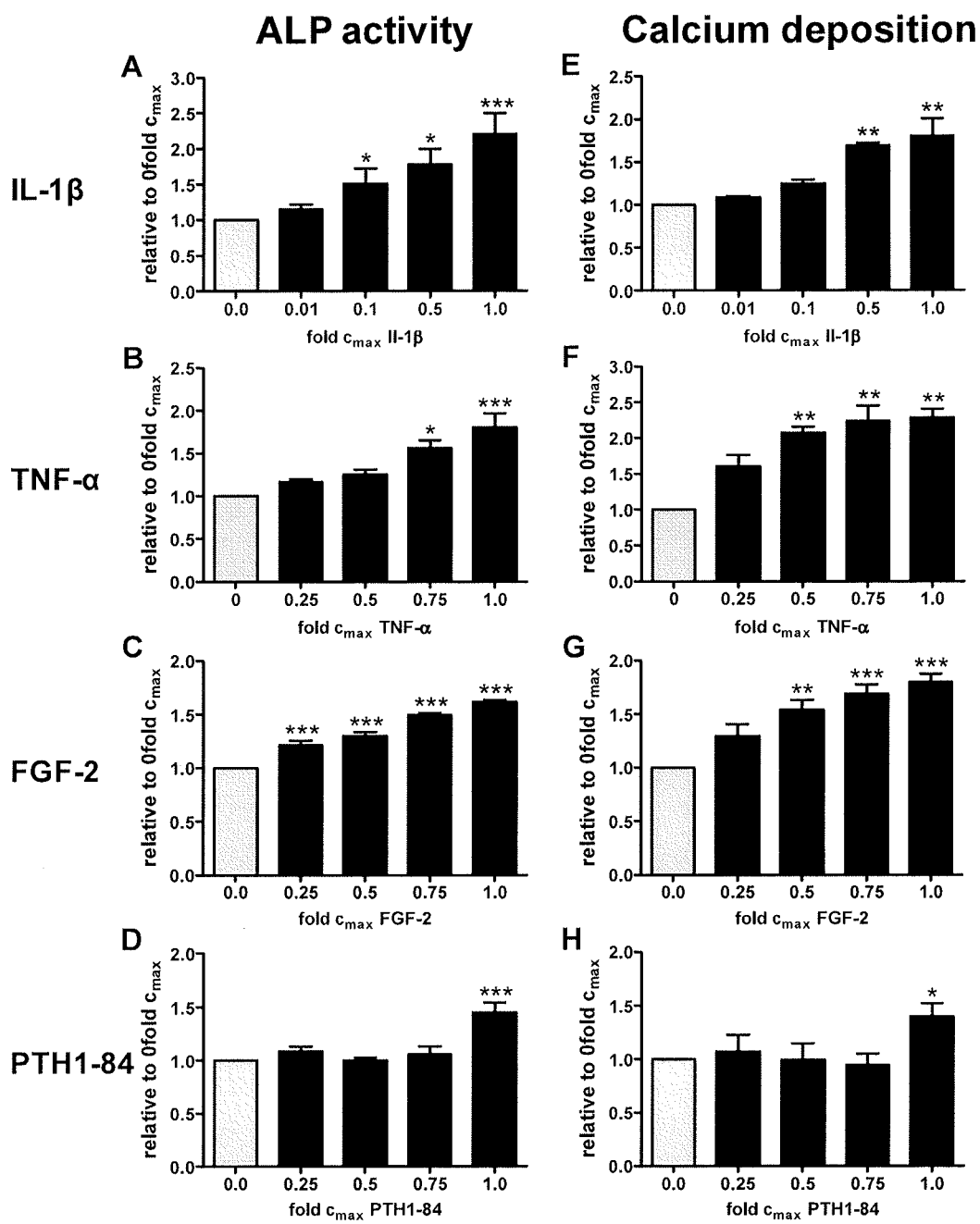
FIG. 5 depicts the dose-dependent induction of osteoblastic differentiation in mesenchymal stromal cells (MSC) by pro-inflammatory cytokines, fibroblast growth factors (FGF), and full-length parathyroid hormone (PTH1-84). (A-E) Alkaline phosphatase (ALP) activity in MSCs treated with different concentrations of IL-1β (A), TNF-α (B), FGF-2 (C), FGF-23 (D) or PTH1-84 (E) in osteoblast induction medium (OM) for 7 days. (F-J) Calcium deposited by MSCs cultured for 3 weeks in OM with increasing concentrations of IL-1β (F), TNF-α (G), FGF-2 (H), FGF-23 (I) or PTH1-84 (J). "Fold CMAX" denotes the x-fold concentration of the highest reported concentration found in dialysis patients (IL-1β CMAX=1.7 µg/L; TNF-α CMAX=408 ng/L; FGF-2 CMAX=19.5 ng/L; FGF-23 CMAX=255.2 ng/L; PTH1-84 CMAX=2.4 µg/L). ALP activity and calcium were normalized to sample protein content. All values are expressed relative to OM without cytokine (set 1.00). Means+SEM from 4-6 independent experiments are shown. *P<0.05, P<0.01, *P<0.001.

The concentrations of certain molecules found in a dialysis patient and which are deemed to play a role in the mediation of vascular calcification are sometimes extremely high and will not be encountered frequently in stable patients on maintenance dialysis. Therefore, in order to get an insight on dose effects of certain mediators on the development of calcification, it was tested whether or not also lower concentrations of inducers of MSC osteoblast differentiation have detectable effects at least in the present in vitro model (Example 4). Dose-dependent increases were identified in both, ALP activity and calcium deposition induced by the pro-inflammatory cytokines IL-1β (FIGS. 5, A and E) and TNF-α (FIGS. 5, B and F). The dose-response curve for FGF-2 also revealed induction of osteoblastic differentiation and calcium deposition at concentrations below $C_{MAX}$ (FIGS. 5, C and G). It is obvious from these results that high cut-off membranes according to the invention that high cut-off dialyzers will have an effect not only in high risk patients or those patients who already suffer from severe vascular calcification, but also on patients who have not yet developed a severe vascular calcification and/or do not show high levels of mediators suspected of inducing vascular calcification. In the latter case, the onset and development of vascular calcification can be prevented or delayed.

Figure 2:
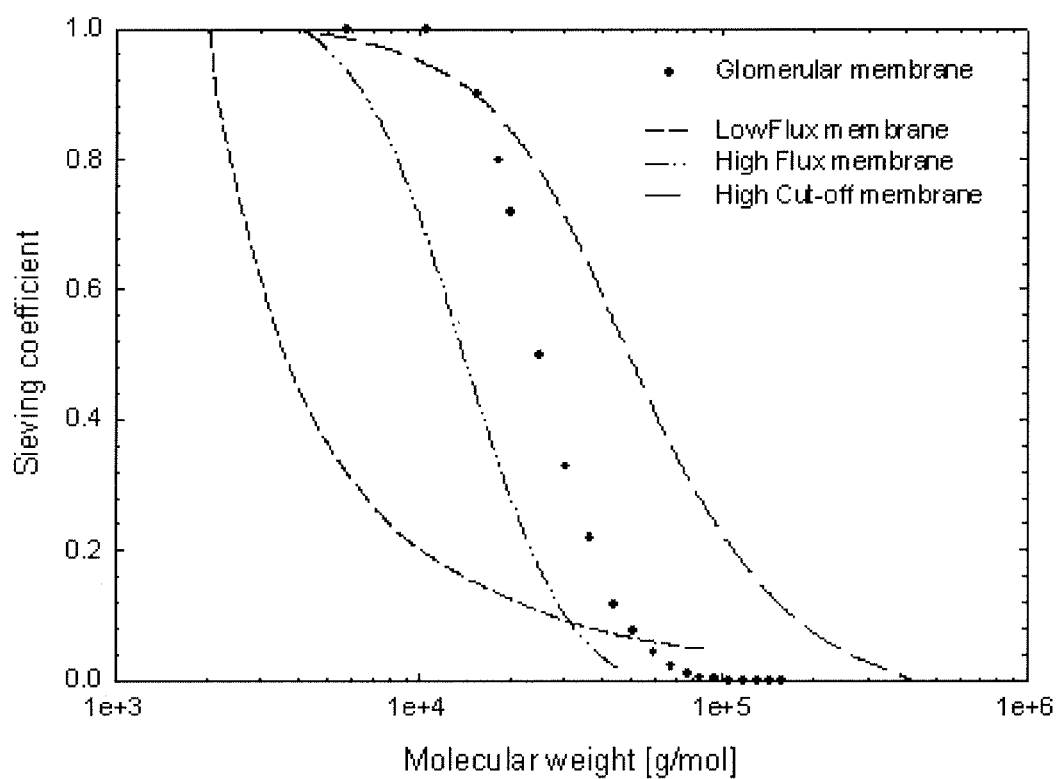
FIG. 2 shows characteristic dextran sieving curves for the different types of dialysis membranes: low flux, high flux and high cut-off. The data for the glomerular membrane (as reported by Axelsson et al. (2009): Loss of size selectivity of the glomerular filtration barrier in rats following laparotomy and muscle trauma. *American Journal of Physiology—Renal Physiology*, 297, F577-F582) has been added for illustration.
Figure 3:
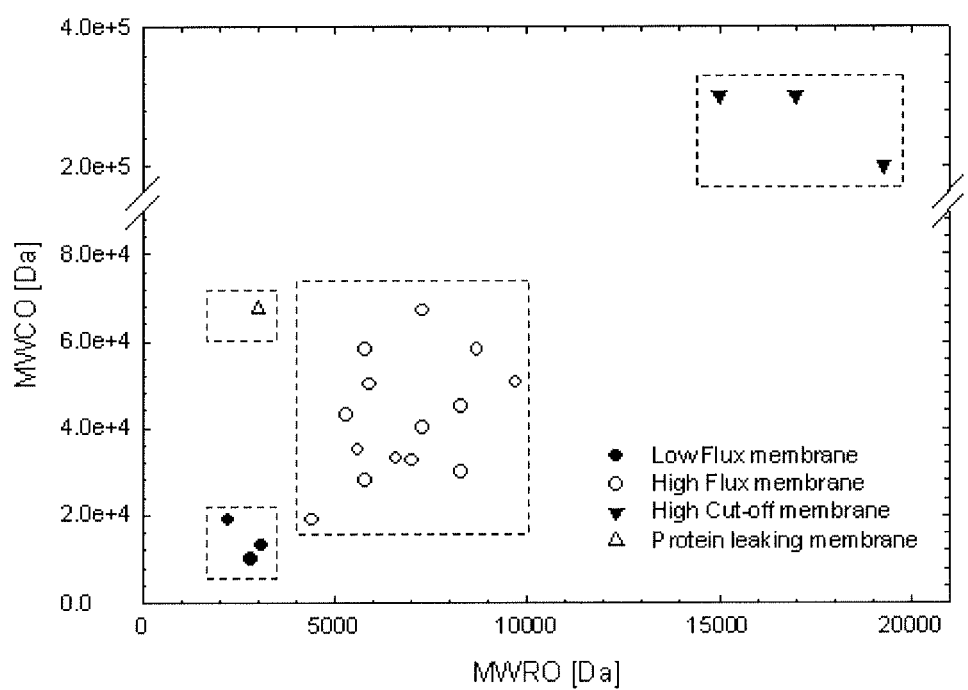
FIG. 3 shows a mapping of different types of blood membranes based on the molecular weight retention onset and molecular weight cut-off from dextran sieving curves. The dotted line squares approximately represent the boundaries that delimit the dialyzer families.

As can be seen from FIG. 2, the high cut-off dialysis membrane allows for the limited passage, in whole blood, of molecules with a molecular weight of above 60 kD, including also, to a certain limited extend, albumin with a molecular weight of 68 kD. High-flux membranes, in contrast, allow only for the passage of molecules up to 25kD in whole blood. For this reason, filters based on and comprising high cut-off membranes can be efficiently used to remove larger molecules in the range of between 25 and 60 kD, which cannot be efficiently addressed with conventional dialysis based on low flux or high flux dialyzer.

It was thus found, in the present invention, that in hemodialysis patients with CKD stages 3-5 and with an Agatston score of 11 and more, the use of high cut-off or medium cut-off membranes leads to a reduction of mediators inducing and/or governing vascular calcification in CKD patients. Said use thus leads to an effective treatment of patients suffering from vascular calcification and/or to an improved, preventive treatment of patients having a moderate to high risk of developing vascular calcification and related cardiovascular diseases, respectively.

The use of high cut-off or medium cut-off membranes for treating hemodialysis patients was found to be especially favorable for patients with CKD stages 3-5 and with an Agatston score of >100 to 400. The treatment according to the invention is especially indicated for patients with CKD stages 3-5 and with an Agatston score of >400. The use of the high cut-off or medium cut-off membrane in the dialysis treatment of patients of Agatston scores of 11-100, 100-400 and >400 is also very advisable for patients with CKD stages 4-5. The use according to the invention of high cut-off or medium cut-off membranes in the treatment of hemodialysis patients is especially indicated for patients with CKD stage 5 and an Agatston score of >100.

The expression "vascular calcification" as used herein refers to the process of dedifferentiation or transformation of vascular smooth muscle cells (VSMC) into osteo/chondrocytic-like cells, whereupon osteo/chondrocytic-like VSMC become calcified in a process similar to bone formation. The calcification involves deposition of collagen and noncollagenous proteins in the intima or media and incorporation of calcium and phosphorus into matrix vesicles to initiate mineralization and further mineralization into hydroxyapatite. The expression "vascular calcification" thus encompasses, on a clinical level, arterial stiffening, higher pulse wave velocity (PWV), earlier return of wave reflections from the periphery to the ascending aorta during systole and significant increase of aortic systolic blood pressure with reduced diastolic blood pressure and high pulse pressure. The vascular calcification is quantitatively described by determining the Coronary Artery Calcification Score (CACS) as detectable by electron-beam or multislice computed tomography (CT) and as described before. For the avoidance of doubt, the expression "Agatston score" as used herein is equivalent to the expression Coronary Artery Calcification Score (CACS) as used herein.

In the context of the present invention, the expression "CKD patients" refers to patients with CKD (KDOQI) stages 3-5, if not indicated otherwise. Stage 3 refers to moderately reduced kidney function with GFR (Glomerular Filtration Rate, normalized to an average surface area (size) of 1.73 m$^2$) values of 45-59 (3A) and 30-44 (3B). Stage 4 refers to severely reduced kidney function with GFR values of 15-29. Stage 5 refers to very severe or endstage kidney failure and GFR values below 15.

The expression "high cut-off membrane" or "high cut-off membranes" as used herein refers to membranes comprising at least one hydrophobic polymer and at least one hydrophilic polymer and having a MWRO of between 15 and 20 kD and a MWCO of between 170-320 kD. The membranes can also be characterized by a pore radius, on the selective layer surface of the membrane, of between 8-12 nm. The expression "medium cut-off membrane" as used herein refers to membranes comprising at least one hydrophobic polymer and at least one hydrophilic polymer and having a MWRO of between 8.5 and 14.0 kD and a MWCO of between 55 kD and 130 kD. The membranes can also be characterized by a pore radius, on the selective layer surface of the membrane, of above 5.5 nm and below 8.0 nm. For the avoidance of doubt, the determination of MWRO and MWCO for a given membrane is according to the methods of Boschetti-de-Fierro et al. (2013); see "Materials and Methods" section of the reference. The expression "high cut-off membrane" as used herein otherwise comprises membranes characterized by the performance parameters as shown in Table I of this document, without wanting to limit the definition of high cut-off membranes to the single performance parameters disclosed in Table I for said membranes. The high cut-off or medium cut-off membranes can be processed into hemodialysis filters by methods generally known in the art, for example, into hemodialysis filters having a design in terms of housing, area, fiber and bundle geometry, packing density and flow characteristics, similar to or the same as products already available on the market such as, for example, HCO1100® or Theralite®, both comprising high cut-off membranes. Accordingly, the use of the expression "high cut-off membrane" or "medium cut-off membrane" in the context of the present invention encompasses the use of the membrane within an adequate filter device fit for being used in/on an extracorporeal dialysis machine.

In one embodiment of the invention, the high cut-off membranes for the treatment of vascular calcification are characterized by a pore radius, on the selective surface layer of the membrane, of between 8-12 nm.

In a further embodiment of the invention, the high cut-off dialysis membrane is characterized by a clearance (ml/min) for κ-FLC of from 35 to 40, and for κ-FLC of from 30 to 40 as determined according to the method described in Table I.

In yet another embodiment of the invention, the high cut-off dialysis membranes for the treatment of vascular calcification are characterized by allowing the passage of molecules having a molecular weight of up to 45 kDa with a sieving coefficient of from 0.1 to 1.0 in presence of whole blood, based on EN1238 with $Q_B$ max and UF 20%.

In yet another embodiment of the invention, the high cut-off dialysis membrane is characterized by sieving coefficients of from 0.9 to 1.0 for β$_2$-microglobulin and of from 0.8 to 1.0 for myoglobin, when measured according to EN 1283 with $Q_B$ max and UF 20%.

In yet another embodiment of the invention, the medium cut-off dialysis membrane is characterized as set forth in European Patent Application No. 14154175.5.

It is a further object of the present invention to provide for a method for reducing and/or preventing vascular calcification in hemodialysis patients having an Agatston score of more than 11, comprising withdrawing and bypassing the blood from the patient in a continuous flow into contact with one face of an hemodialysis membrane, simultaneously passing dialysate solution in a continuous flow on an opposite face of the hemodialysis membrane to the side of the hemodialysis membrane in contact with the blood, the flow of the dialysate solution being countercurrent to the direction of flow of blood, and returning the blood into the patient, wherein the hemodialysis membrane is characterized in that it comprises at least one hydrophobic polymer and at least one hydrophilic polymer and has a MWRO of between 15 and 20 kD and a MWCO of between 170-320 kD, or that it comprises at least one hydrophobic polymer and at least one hydrophilic polymer and has a MWRO of between 8.5 and 14 kD and a MWCO of between 55 kD and 130 kD It is a further aspect of the present invention to provide for a method for reducing and/or preventing vascular calcification in hemodialysis patients having an Agatston score of more than 100. It is another aspect of the present invention to provide for a method for reducing and/or preventing vascular calcification in hemodialysis patients having an Agatston score of between 100 and 400. It is yet a another aspect of the present invention to provide for a method for reducing and/or preventing vascular calcification in hemodialysis patients having an Agatston score of more than 400. It is also an aspect of the present invention to provide for a method for reducing and/or preventing vascular calcification in hemodialysis patients having an Agatston score of more than 11 and with CKD stages 3-5, especially 4-5. It is a further aspect of the present invention to provide for a method for reducing and/or preventing vascular calcification in hemodialysis patients having an Agatston score of more than 100 and with CKD stages 4-5, especially 5.

It is another aspect of the present invention to provide for a dialysis membrane comprising at least one hydrophobic polymer and at least one hydrophilic polymer, wherein the membrane allows the passage of molecules having a molecular weight of up to 45 kDa with a sieving coefficient of from 0.1 to 1.0 in presence of whole blood, based on EN1238 with $Q_B$ max and UF 20%, for treating vascular calcification in a hemodialysis patient, especially in hemodialysis patients with an Agatston score of >11.

It is also an aspect of the present invention to provide for a dialysis membrane comprising at least one hydrophobic polymer and at least one hydrophilic polymer, wherein the membrane has a molecular weight retention onset (MWRO) of between 15 and 20 kD and a MWCO of between 170-320 kD for treating vascular calcification in hemodialysis patients, especially in hemodialysis patients with an Agatston score of >11, wherein the membrane has a pore radius, on the selective layer, of between 8 and 12 nm.

It is also an aspect of the present invention to provide for a dialysis membrane comprising at least one hydrophobic polymer and at least one hydrophilic polymer, wherein the membrane has a molecular weight retention onset (MWRO) of between 8.5 kD and 14 kD and a MWCO of between 55 kD and 130 kD for treating vascular calcification in hemodialysis patients, especially in hemodialysis patients with an Agatston score of >11, wherein the membrane has a pore radius, on the selective layer, of between 8 and 12 nm.

In another embodiment of the invention, the hemodialysis treatment regime is performed with a high cut-off or medium cut-off membrane which has a urea clearance of at least 170 ml/min at a $Q_B$ of 200 ml/min and a $Q_D$ of 500 ml/min (UF=0 ml/min). In yet another embodiment of the invention, the dialysis treatment according to the invention must ensure a Kt/V of >1.2.

In yet another embodiment of the invention, a patient's total albumin loss does not exceed about 60 g per week, and preferably does not exceed 40 g per week.

In one embodiment of the invention, the hemodialysis treatment with the membranes according to the invention is performed from 2 to 4 times per week for a period of from 2 to 6 hours, respectively, with a membrane according to the invention. A hemodialysis patient suffering from vascular calcification, especially a CKD patient with stage 3-5, is thus being treated, for a certain period of time, only with such hemodialysis filter according to the invention. In one embodiment of the invention, the treatment may continue until the signs of vascular calcification have been stayed or have decreased. In another embodiment of the invention, the patient receives a continual standard hemodialysis treatment with a hemodialysis filter comprising a medium cut-off membrane. In the context of the present invention, "stayed" and/or "decreased" refers to a constant Agatston score or the reduction of the Agatston score, respectively. According to another embodiment of the invention, the treatment regimen as described may be applied for a period of from 4 to 12 weeks. In yet another embodiment of the invention, the treatment may continually be used for a hemodialysis patient with stage 3-5, especially a patient who belongs to a medium to high or high risk group as defined by the Agatston score.

In another embodiment of the invention, one of three hemodialysis treatments per week is performed for a period of 2 to 6 hours with a membrane according to the invention, whereas two of three hemodialysis treatments per week comprise the use of a standard high-flux hemodialysis membrane. Said treatment may be used in cases where standard dialysis is recommended in addition to using a hemodialysis filter according to the invention. In one embodiment of the invention, the treatment may continue until the signs of vascular calcification have been stayed or have decreased, or until an Agatston score of below 100, preferably below 50 has been reached. In another embodiment of the invention, the treatment regime as described may be applied for a period of from 4 to 12 weeks. In yet another embodiment of the invention, the treatment may continually be used for a hemodialysis patient with CDK stage 3-5, especially a patient who belongs to a medium to high or high risk group as defined by the Agatston score.

In a further embodiment of the present invention, the hemodialysis treatment for a period of 2 to 6 hours is performed with a dialysis filter comprising a membrane according to the invention every other dialysis treatment, whereas the other hemodialysis treatment comprises the use of a standard high-flux hemodialysis membrane. Said treatment may be used in cases where standard dialysis is recommended in addition to using a hemodialysis filter according to the invention. In one embodiment of the invention, the treatment may continue until the signs of vascular calcification have been stayed or have decreased, or until an Agatston score of below 100, preferably below 50 has been reached.

Depending on the specific condition of a patient, such treatment regimens or routines can be applied singularly or dynamically, i.e. they may be interchanged or subsequently be used for certain periods of time.

Accordingly, the above method also provides for a possibility to reduce or suspend the further development of vascular calcification in hemodialysis patients. The treatment according to the invention is designed to reduce or remove such molecules which are connected to the condition of vascular calcification as discussed before. The amelioration of the condition of the patient based on the present treatment will allow reducing medication which has to be administered to the patients and the risk going hand in hand with such medication as described before. The respective reduction rates upon using a high cut-off or medium cut-off membrane according to the invention at least lie in the range of more than 10% relative to the Agatston score determined at the beginning of treating a given patient according to the invention. It is an object of the present invention to achieve reduction rates of more than 20%, preferably more than 30%. At least the use of high cut-off or medium cut-off membranes and filter devices comprising them is connected to no further increase of the Agatston score determined at the beginning of treating a given patient according to the invention.

In one embodiment of the invention, the hemodialysis treatment according to the invention can be supplemented by a state of the art medication which would otherwise be prescribed to a patient suffering from vascular calcification.

Dialysis machines which can be used for performing a treatment according to the invention are standard dialysis machines which can accurately control and monitor the ultrafiltration rate. Examples for such devices are the AK 96™, AK 200™ S and AK 200™ ULTRA S, PrismafleX eXeed™ or the Artis™ dialysis machines of Gambro Lundia AB. However, any other dialysis machine having UF control can also be used for the treatment.

Parameters for performing a treatment according to the invention can be adjusted to standard dialysis treatment or medium cut-off parameters and the specifications of the high cut-off or medium cut-off membrane. Typical flow rates used for the present treatment may vary. It is advantageous to use flow rates with a $Q_B$ (blood flow) of 100-500, preferably 250-400 ml/min and a $Q_D$ (dialysate flow rate) of 100-1000, preferably 300-500 ml/min.

Membrane passage of a solute, such as a protein which needs to be removed from blood, is described by means of the sieving coefficient S. The sieving coefficient S is calculated according to $S=(2C_F)/(C_{Bin}+C_{Bout})$, where $C_F$ is the concentration of the solute in the filtrate and $C_{Bin}$ is the concentration of a solute at the blood inlet side of the device under test, and $C_{Bout}$ is the concentration of a solute at the blood outlet side of the device under test. A sieving coefficient of S=1 indicates unrestricted transport while there is no transport at all at S=0. For a given membrane each solute has its specific sieving coefficient.

In addition, the sieving curves may serve as a basis for determining, for example, the average or mean pore size or pore size distribution of a membrane on the selective layer. There is a factual and mathematical correlation between the sieving characteristics of a membrane and its pore structure. The mean pore size or pore size distribution can, for example, be determined according to Aimar et al (1990) from the dextran sieving curve.

In one embodiment, the membrane allows for the passage of free light chains (FLC). That is, the κ or λ free light chains pass through the membrane. High flux membranes, with smaller pore sizes, sometimes also referred to as "protein-leaking membranes", have been observed to remove some free light chains. However, this appears to be primarily due to binding of the FLC onto the dialysis membranes. FLC may be used as markers of middle molecular weight proteins. Although clearing of free light chains is not a primary target of the invention, their reduction can be used as an indicator of membrane functionality.

It is provided, in a further aspect of the invention, dialysis system wherein the membrane has a clearance (ml/min) for κ-FLC of from 30 to 45, and for λ-FLC of from 28 to 40. Clearance is determined in vitro (±20%) with $Q_B$=250 ml/min, $Q_D$=500 ml/min, UF=0 ml/min in bovine plasma having a protein level of 60 g/l at 37° C. The plasma level for human κ=500 mg/l and for human λ=250 mg/l.

In one aspect of the present invention, the dialysis membrane according to the invention comprises at least one hydrophilic polymer and at least one hydrophobic polymer. In one embodiment, at least one hydrophilic polymer and at least one hydrophobic polymer are present in the dialysis membrane as domains on the surface of the dialysis membrane.

The hydrophobic polymer may be chosen from the group consisting of polyarylethersulfone (PAES), polypropylene (PP), polysulfone (PSU), polymethylmethacrylate (PMMA), polycarbonate (PC), polyacrylonitrile (PAN), polyamide (PA), polytetrafluorethylene (PTFE) or combinations thereof. In one embodiment of the invention, the hydrophobic polymer is chosen from the group consisting of polyarylethersulfone (PAES), polypropylene (PP), polysulfone (PSU), polycarbonate (PC), polyacrylonitrile (PAN), polyamide (PA) polytetrafluorethylene (PTFE) or combinations thereof. In another embodiment of the invention, the hydrophobic polymer is chosen from the group consisting of polyarylethersulfone (PAES) and polysulfone (PSU).

The hydrophilic polymer may be chosen from the group consisting of polyvinylpyrrolidone (PVP), polyethyleneglycol (PEG), polyvinylalcohol (PVA), and copolymer of polypropyleneoxide and polyethyleneoxide (PPO-PEO). In one embodiment of the invention, the hydrophilic polymer may be chosen from the group consisting of polyvinylpyrrolidone (PVP), polyethyleneglycol (PEG) and polyvinylalcohol (PVA). In one embodiment of the invention, the hydrophilic polymer is polyvinylpyrrolidone (PVP).

Figure 6:
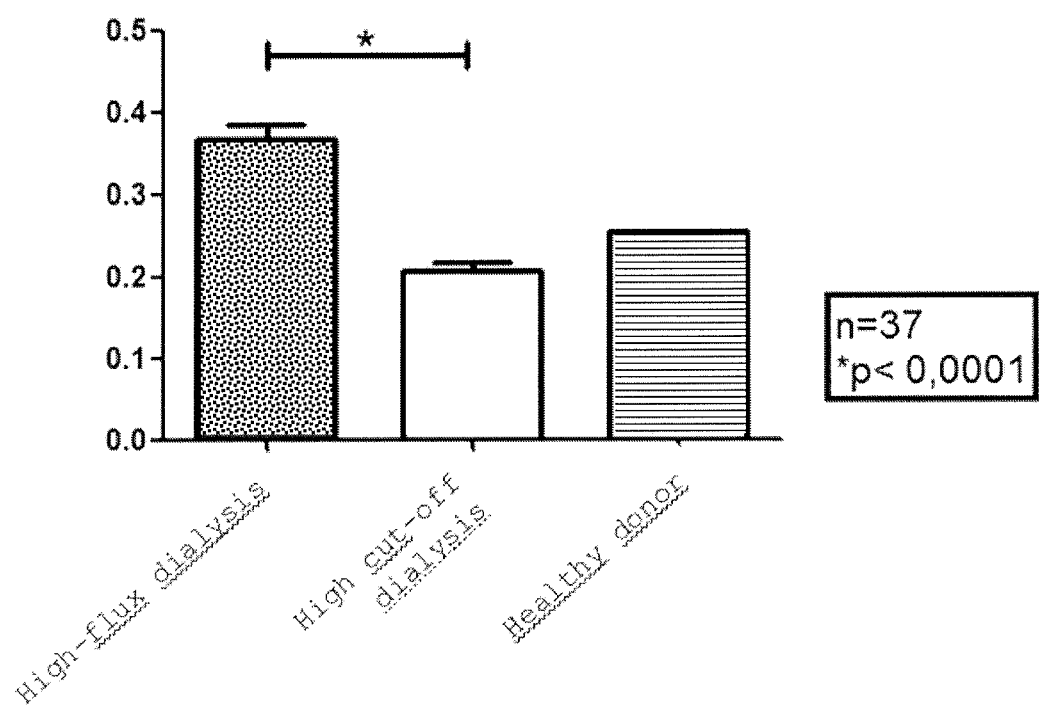
FIG. 6 shows the relative calcification which was measured in vitro in vascular smooth muscle cells (VSMC) upon incubation with plasma samples from healthy donors or from 48 patients who were dialysed with both high-flux and high cut-off membranes for three weeks (Example 3.6). Calcification was assessed after 10 days with alkaline phosphatase and alizarin staining. A reduction of calcification was measured in VSMC incubated with serum after the high cut-off phase compared to the high-flux phase.

In one embodiment of the invention, the high cut-off dialysis membrane is a hollow fiber having a symmetric (sponge-like) or an asymmetric structure with a separation layer present in the innermost layer of the hollow fiber. In one embodiment of the invention, the high cut-off dialysis membrane has at least a 3-layer asymmetric structure, wherein the separation layer has a thickness of less than 0.5 μm. In one embodiment, the separation layer contains pore channels having an average pore size of more than 7 nm, generally between 8 and 12 nm as based on dextran sieving coefficients (see also Boschetti-de-Fierreo et al. (2013), Table III). The average pore size (diameter) is generally above 8 nm for this type of membrane (FIG. 6). The next layer in the hollow fiber membrane is the second layer, having the form of a sponge structure and serving as a support for said first layer. In a preferred embodiment, the second layer has a thickness of about 1 to 15 μm. The third layer has the form of a finger structure. Like a framework, it provides mechanical stability on the one hand; on the other hand a very low resistance to the transport of molecules through the membrane, due to the high volume of voids. During the transport process, the voids are filled with water and the water gives a lower resistance against diffusion and convection than a matrix with a sponge-filled structure having a lower void volume. Accordingly, the third layer provides mechanical stability to the membrane and, in a preferred embodiment, has a thickness of 20 to 60 µm.

In one embodiment, the high cut-off dialysis membrane also includes a fourth layer, which is the outer surface of the hollow fiber membrane. In this embodiment, the outer surface has openings of pores in the range of 0.5 to 3 µm and the number of said pores is in the range of from 10.000 to 150.000 pores/mm$^2$, preferably 20.000 to 100.000 pores/mm$^2$. This fourth layer preferably has a thickness of 1 to 10 µm.

The manufacturing of a high cut-off dialysis membrane follows a phase inversion process, wherein a polymer or a mixture of polymers is dissolved in a solvent to form a polymer solution. The solution is degassed and filtered and is thereafter kept at an elevated temperature. Subsequently, the polymer solution is extruded through a spinning nozzle (for hollow fibers) or a slit nozzle (for a flat film) into a fluid bath containing a non-solvent for the polymer. The non-solvent replaces the solvent and thus the polymer is precipitated to an inverted solid phase.

To prepare a hollow fiber membrane, the polymer solution preferably is extruded through an outer ring slit of a nozzle having two concentric openings. Simultaneously, a center fluid is extruded through an inner opening of the nozzle. At the outlet of the spinning nozzle, the center fluid comes in contact with the polymer solution and at this time the precipitation is initialized. The precipitation process is an exchange of the solvent from the polymer solution with the non-solvent of the center fluid.

By means of this exchange the polymer solution inverses its phase from the fluid into a solid phase. In the solid phase the pore structure, i.e. asymmetry and the pore size distribution, is generated by the kinetics of the solvent/non-solvent exchange. The process works at a certain temperature which influences the viscosity of the polymer solution. The temperature at the spinning nozzle and the temperature of the polymer solution and center fluid is 30 to 80° C. The viscosity determines the kinetics of the pore-forming process through the exchange of solvent with non-solvent. The temperature in the given range should be chosen in way to be some degrees higher than the temperature which would have been chosen for the same recipe in order to obtain a standard high-flux membrane. Subsequently, the membrane is preferably washed and dried.

By the selection of precipitation conditions, e. g. temperature and speed, the hydrophobic and hydrophilic polymers are "frozen" in such a way that a certain amount of hydrophilic end groups are located at the surface of the pores and create hydrophilic domains. The hydrophobic polymer builds other domains. A certain amount of hydrophilic domains at the pore surface area are needed to avoid adsorption of proteins. The size of the hydrophilic domains should preferably be within the range of 20 to 50 nm. In order to repel albumin from the membrane surface, the hydrophilic domains also need to be within a certain distance from each other. By the repulsion of albumin from the membrane surface, direct contact of albumin with the hydrophobic polymer, and consequently the absorption of albumin, are avoided.

The polymer solution used for preparing the membrane preferably comprises 10 to 20 wt.-% of hydrophobic polymer and 2 to 11 wt.-% of hydrophilic polymer. The center fluid generally comprises 45 to 60 wt.-% of precipitation medium, chosen from water, glycerol and other alcohols, and 40 to 55 wt.-% of solvent. In other words, the center fluid does not comprise any hydrophilic polymer.

In one embodiment, the polymer solution coming out through the outer slit openings is, on the outside of the precipitating fiber, exposed to a humid steam/air mixture. Preferably, the humid steam/air mixture has a temperature of at least 15° C., more preferably at least 30° C., and not more than 75° C., more preferably not more than 60° C.

Preferably, the relative humidity in the humid steam/air mixture is between 60 and 100%. Furthermore, the humid steam in the outer atmosphere surrounding the polymer solution emerging through the outer slit openings preferably includes a solvent. The solvent content in the humid steam/air mixture is preferably between 0.5 and 5.0 wt.-%, related to the water content. The effect of the solvent in the temperature-controlled steam atmosphere is to control the speed of precipitation of the fibers. When less solvent is employed, the outer surface will obtain a denser surface, and when more solvent is used, the outer surface will have a more open structure. By controlling the amount of solvent within the temperature-controlled steam atmosphere surrounding the precipitating membrane, the amount and size of the pores on the outer surface of the membrane are controlled, i.e. the size of the openings of the pores is in the range of from 0.5 to 3 µm and the number of said pores is in the range of from 10,000 to 150,000 pores/mm$^2$. A fourth layer of a high cut-off dialysis membrane is preferably prepared by this method.

Before the extrusion, suitable additives may be added to the polymer solution. The additives are used to form a proper pore structure and optimize the membrane permeability, the hydraulic and diffusive permeability, and the sieving properties. In a preferred embodiment, the polymer solution contains 0.5 to 7.5 wt.-% of a suitable additive, preferably chosen from the group comprising water, glycerol and other alcohols.

The solvent may be chosen from the group comprising N-methylpyrrolidone (NMP), dimethyl acetamide (DMAC), dimethyl sulfoxide (DMSO) dimethyl formamide (DMF), butyrolactone and mixtures of said solvents.

Medium cut-off membranes can be prepared as described in EP 14154175.5.

Membranes which can also effectively be used according to the invention and methods for preparing them are also described in EP 2 253 367 A1. Dialysis filters which can be used according to the invention are shown, for example, in Table II of Boschetti-de-Fierro et al (2013) and identified as "High cut-off" dialyzer.

It will be readily apparent to one skilled in the art that various substitutions and modifications may be made to the invention disclosed herein without departing from the scope and spirit of the invention.

The present invention will now be illustrated by way of non-limiting examples in order to further facilitate the understanding of the invention.

EXAMPLES

Example 1

High Cut-Off Membrane Preparation

Two solutions are used for the formation of the membrane, the polymer solution consisting of hydrophobic and hydrophilic polymer components (21 wt-%) dissolved in N-methyl-pyrrolidone, and the center solution being a mixture of N-methyl-pyrrolidone and water. The polymer solution contains polyethersulfone (PES 14.0 wt-%) and polyvinylpyrrolidone (PVP 7.0 wt-%) as membrane building components. The solution further contains NMP (77.0 wt-%)

and water (2.0 wt-%). The center solution contains water (53.0 wt-%) and NMP (47.0 wt-%).

During the membrane formation process polymer and center solution are brought in contact with a spinneret or jet and the membrane precipitates. A defined and constant temperature (58° C.) is used to support the process. The precipitated hollow fiber falls through a humidified shaft filled with steam (100% relative humidity, 54° C.) into a washing bath (20° C., ~4 wt-% NMP). The membrane is further washed in two additional water baths (70° C.-90° C.) with counter current flow (250 l/h). Membrane drying is performed online, wherein remaining water is removed.

Fibers used in the following tests had an inner diameter of 215 µm, a wall thickness of 50 µm, and an effective membrane area of, for example 1.1 m² (as in HCO1100®) or 2.1 m² (as in Theralite®).

Example 2

Preparation of Hand Bundles, Mini-Modules and Filters

The preparation of a membrane bundle after the spinning process is necessary to prepare the fiber bundle for following performance tests with mini-modules. The first process step is to cut the fiber bundles to a defined length of 23 cm. The next process step consists of melting the ends of the fibers. An optical control ensures that all fibers are well melted. Then, the ends of the fiber bundle are transferred into a potting cap. The potting cap is fixed mechanically and a potting tube is put over the potting caps. Then the fibers are potted with polyurethane. After the polyurethane has hardened, the potted membrane bundle is cut to a defined length and stored dry before it is used for the different performance tests.

Mini-modules [=fiber bundles in a housing] are prepared in a similar manner. The mini-modules ensure protection of the fibers and are used for steam-sterilization. The manufacturing of the mini-modules comprises the following specific steps:
(A) The number of fibers required is calculated for an effective surface A of 360 cm² according to equation (1)

$$A = \pi \times d_i \times l \times n [\text{cm}^2] \quad (1)$$

Wherein $d_i$ is the inner diameter of fiber [cm], n represents the amount of fibers, and l represents the effective fiber length [cm].
(B) The fiber bundle is cut to a defined length of 20 cm.
(C) The fiber bundle is transferred into the housing before the melting process
(D) The mini-module is put into a vacuum drying oven over night before the potting process.

For in vivo studies standard format dialysis filters are needed. Such filters can be prepared from the hollow fiber membranes of Example 1 according to methods known in the art. Fiber geometry is as said before in Example 1. The blood flow range can be from 100-400 ml/min. For example, the HCO1100® dialyzer has a blood flow range of 200-500 ml/min, the Theralite® dialyzer has a blood flow range of 100 to 400 ml/min. Dialysate flow range is from 300 to 800 ml/min. For example, the HCO1100® dialyzer has a dialysate flow range of 300-800 ml/min, the Theralite® dialyzer has a dialysate flow range of up to 800 ml/min.

Example 3

Effects of Dialysis with High Cut-Off Membranes on the Ability of Serum to Induce Osteoblastic Differentiation in MSCs The study was conducted in accordance with the Declaration of Helsinki and had been approved by local ethic authorities. All subjects provided written informed consent.

3.1 Isolation and Culture of MSCs

MSCs were isolated from bone marrow aspirates obtained from 20 healthy bone marrow donors (7 female, 13 male) median age 31 years (range 0.5-42) as described previously (Lange et al. (2007), *J Cell Physiol* 213, 18-26). All subjects provided written informed consent. In brief, bone marrow mononuclear cells were purified by Percoll density gradient centrifugation, plated at 400,000 cells/cm² and cultured in α-MEM (#E15-862, PAA) supplemented with 100 U/mL penicillin (PAA), 100 µg/mL streptomycin (PAA), 2 IU/ml heparin (Ratiopharm), and 5% freshly thawed platelet lysate at 37° C. and 5% $CO_2$. Nonadherent cells were washed off with PBS after 2-3 days. Medium was changed twice a week. When cultures reached about 90% confluence, cells were detached with 0.05% Trypsin/0.02% EDTA (PAA), counted, and re-plated at 500 cells/cm² in 175 cm² flasks (Saarstedt). For all MSC preparations, mesenchymal multilineage differentiation capacity, expression of characteristic surface marker proteins (CD59, CD90, CD105), and lack of hematopoetic markers were confirmed (supplemental Figure S1) according to the standard criteria for MSC research.

3.2 Induction of Osteoblastic Differentiation

Passages 2 to 5 were used for experiments. MSCs were seeded in complete α-MEM at 141,000 cells per well in 6-well-plates. The next day, medium was changed to osteoblast induction medium (OM) consisting of Dulbecco's Modified Eagle's Medium (DMEM; PAA) supplemented with 2 mM glutamine (PAA), penicillin/streptomycin (PAA), 1% FCS (Biochrome), 10 mM β-glycerophosphate, 500 µM ascorbic acid, and 100 nM dexamethasone (all from Sigma).

3.3 High Cut-Off Versus Conventional Dialysis Membranes

For the assessment of enhanced removal of relevant mediators of vascular calcification by dialysis and the effects on MSC osteoblastic differentiation, serum from 16 dialysis patients treated with either conventional (Polyflux 210H, Gambro) or high cut-off membranes according to the invention (HCO1100®, in line with a Polyflux® 14L dialyzer for reaching a sufficient Kt/V due to the limited membrane area of the HCO1100® dialyzer) were tested. Serum was obtained immediately before a dialysis session after a dialysis-free interval of 3 days. One serum sample was taken after at least 3 weeks of dialysis treatment with the conventional high-flux (HFL) membrane. Another serum sample was drawn from the same patients after they had been dialyzed for 3 weeks with high cut-off membranes. One half of the patients were treated with the HFL dialyzer prior to the high cut-off dialyzer. The other half received the different treatments in opposite sequence. OM was supplemented with 2.5% patient serum instead of 1% FCS. Medium was changed every 2-3 days.

3.4 Alkaline Phosphatase Activity

Activity of alkaline phosphatase (ALP) in MSCs was determined after exposure to the different experimental conditions for 7 days. Cells were washed with PBS and lysed with 400 µl ALP lysis buffer (150 mM Tris pH 10.0, 0.1 mM $ZnCl_2$, 0.1 mM $MgCl_2$, 1% Triton-X100) at room temperature under constant agitation for 30 minutes. Supernatants were collected and aliquots were immediately frozen at −80° C. For measurement of ALP activity, an aliquot was thawed and centrifuged for 10 min at 12,000 rpm and 4° C. Each sample was measured in triplicate. 50 µl per well of a 96-well-plate were mixed with 200 µl substrate solution (ALP buffer with freshly dissolved p-Nitrophenyl phosphate at 2.7 mM) that was pre-warmed to 37° C. Optical densities (OD) were measured at 405 nm and followed every 10 min over a 1-h incubation period at 37° C. DOD values to baseline ODs at one chosen time point during the linear phase were divided by the protein concentration of the sample as determined with the DC Protein Assay (Bio-Rad). Each LOD/protein ratio was related to the ΔOD/protein ratio of the appropriate control.

3.5 Calcium Deposition

Extracellular calcium deposition by differentiating MSCs was assessed after 3 weeks of incubation with OM and different experimental substances or earlier if the cells started dying due to extensive calcification. After supernatants were discarded calcified cells were scraped off in 500 µL 0.6 M HCl, transferred to microtubes and incubated overnight under constant agitation at 4° C. to solubilize the calcium. Samples were then centrifuged for 60 min at 20,000 g and 4° C. Supernatants were transferred to new microtubes and pellets were dissolved in 25 µl 0.1 M NaOH/0.1% SDS solution for protein quantification with the DC protein assay (Bio-Rad). Supernatants were assayed in duplicate in 96-well-plates. 10 µL either of a calcium standard curve ranging from 5 to 25 mg/dL or sample were mixed with 150 µL color reagent (0.1 mg/mL ortho-cresolphthalein complexone, 1 mg/mL 8-hydroxy-quinoline, 0.7 M HCl) and 150 µl AMP buffer (15% 2-amino-2-methyl-1-propanol in $H_2O$, pH 10.7, adjusted with HCl). After incubation for 15 min at room temperature OD was measured at 540 nm. Blank absorption was subtracted and calcium concentrations were calculated by means of the standard curve. Extracellular calcium was finally expressed as µg calcium per mg protein.

3.5 Statistics

All data are expressed as mean+SEM. The screening experiments were evaluated with the Wilcoxon signed-rank test or, after confirming normal distribution of the data with the Kolmogorov-Smirnov test, with the t-test. 1-way ANOVA followed by Dunnett's post-test was used to evaluate dose-response curves. The Wilcoxon matched pairs test was performed to compare the effect of the two dialysis membranes. All analyses were performed with GraphPad Prism version 5.02 for Windows, GraphPad Software, San Diego Calif. USA. Significance was considered at a value of $p<0.05$.

3.6 In Vitro Calcification of VSMC

During the study 48 patients were dialyzed with both high-flux and high cut-off membranes for three weeks. After each phase plasma serum samples were drawn and incubated with calcifying smooth muscle cells as described before. After ten days calcification was assessed with alkaline phosphatase and alizarin staining. A reduction of calcification was measured in VSMC which had been incubated with serum after the high cut-off phase compared to high-flux phase (FIG. 6).

Figure 7:
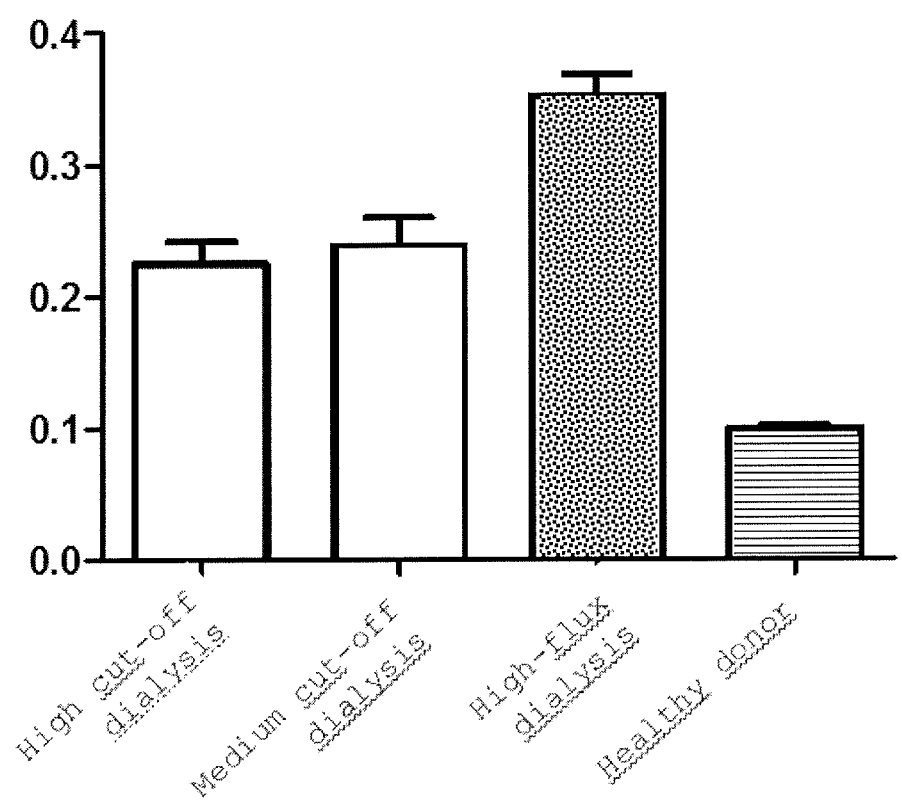
FIG. 7 shows the relative calcification of VSMC upon incubation with plasma samples from healthy donors and from samples obtained from in vitro dialysis experiments with high cut-off, medium cut-off and high-flux membranes, respectively. The results of the in vitro study support the observation of the clinical trial (FIG. 6, Example 3.6). Vascular calcification was reduced by 36% in high cut-off probes and by 32% in medium cut-off probes compared to high-flux probes.

Apart from the clinical trial an in vitro dialysis model was established. Briefly, plasma samples were obtained from healthy donors and incubated with lipopolysacharide for 3 hours. Afterwards the plasma samples were dialyzed with high cut-off, high-flux and medium cut-off membranes in an in vitro model. The plasma samples obtained were incubated in the cell culture model described above. The incubation of VSMC with plasma samples from the in vitro dialysis supports the observations of the clinical trial. Vascular calcification was reduced by 36% with high cut-off probes and by 32% with medium cut-off probes compared to high flux dialysis (FIG. 7).

The invention claimed is:

1. A method of reducing induction of mesenchymal stromal cells in blood, said method comprising the step of contacting the blood with one face of a hemodialysis membrane, simultaneously passing dialysate solution in a continuous flow on an opposite face of the hemodialysis membrane to the side of the hemodialysis membrane in contact with the blood, the flow of the dialysate solution being countercurrent to the direction of flow of blood, wherein the hemodialysis membrane comprises at least one hydrophobic polymer and at least one hydrophilic polymer and has a Molecular Weight Retention Onset (MWRO) of between 15 and 20 kD and a Molecular Weight Cut-Off (MWCO) of between 170-320 kD as determined by dextran sieving before blood contact of the membrane, and wherein the step of contacting the blood with the hemodialysis membrane reduces the induction of the mesenchymal stromal cells.

2. The method of claim 1, wherein the reduction of induction is a reduced induction of osteoblastic phenotype of the mesenchymal stromal cells.

3. The method of claim 1, wherein the reduction of induction is a reduced induction of osteoblastic differentiation of the mesenchymal stromal cells.

4. The method of claim 1, wherein the reduction of induction is a reduced induction of mesenchymal stromal cell calcification.

5. The method of claim 1, wherein the hemodialysis membrane has a MWRO of between 8.5 kD and 14.0 kD and a MWCO of between 55 kD and 130 kD as determined by dextran sieving before blood contact of the membrane.

6. The method of claim 1, wherein the hemodialysis membrane has a pore radius, on the selective layer surface of the membrane, of between 8-12 nm.

7. The method of claim 1, wherein the hemodialysis membrane has a pore radius, on the selective layer surface of the membrane, of more than 5.5 nm and less than 8.0 nm.

8. The method of claim 1, wherein the hemodialysis membrane allows passage of molecules having a molecular weight of up to 45 kDa with a sieving coefficient of from 0.1 to 1.0 in presence of whole blood, based on EN1238 with $Q_B$ max and UF 20%.

9. The method of claim 1, wherein the membrane has a clearance (ml/min) for κ-free light chains (κ-FLC) of from 30 to 45.

10. The method of claim 1, wherein the membrane has a clearance (ml/min) for λ-free light chains (λ-FLC) of from 28 to 40.

11. The method of claim 1, wherein the blood is obtained from a hemodialysis patient.

12. The method of claim 5, wherein the blood is obtained from a hemodialysis patient.

13. The method of claim 6, wherein the blood is obtained from a hemodialysis patient.

14. The method of claim 11, wherein the hemodialysis patient is classified in one of Chronic Kidney Disease (CKD) stages 3, 4 or 5 and has an Agatston score of above 10.

15. The method of claim 11, wherein the hemodialysis patient is classified in one of Chronic Kidney Disease (CKD) stages 4 or 5 and has an Agatston score of above 100.

16. The method of claim 11, wherein the hemodialysis patient undergoes hemodialysis treatment performed from 2 to 4 times per week for a period of from 2 to 6 hours.

17. The method of claim 11, wherein the hemodialysis patient has an Agatston score of above 10.

18. The method of claim 11, wherein the membrane has a reduction rate of the patient Agatston score of more than 10%.

19. The method of claim 11, wherein the membrane has a reduction rate of the patient Agatston score of more than 20%.

20. The method of claim 11, wherein the membrane has a reduction rate of the patient Agatston score of more than 30%.

* * * * *